United States Patent [19]

Marinak et al.

[11] Patent Number: 4,563,531

[45] Date of Patent: Jan. 7, 1986

[54] PROCESS FOR PRODUCING 2,3,5-TRICHLOROPYRIDINE

[75] Inventors: Michael J. Marinak, Kelso; John L. Simonson, Yakima, both of Wash.

[73] Assignee: Kalama Chemical Inc., Kalama, Wash.

[21] Appl. No.: 593,373

[22] Filed: Mar. 26, 1984

Related U.S. Application Data

[63] Continuation-in-part of Ser. No. 422,752, Sep. 24, 1982, abandoned.

[51] Int. Cl.$^4$ ............................................. C07D 213/61
[52] U.S. Cl. ..................................................... 546/345
[58] Field of Search ......................................... 546/345

[56] References Cited

U.S. PATENT DOCUMENTS

| | | | |
|---|---|---|---|
| 3,186,994 | 6/1965 | Johnston et al. | 546/345 |
| 3,418,323 | 12/1968 | Johnston et al. | 546/345 |
| 4,092,151 | 5/1978 | Takahashi et al. | 546/345 |
| 4,275,212 | 6/1981 | Orvik | 546/345 |
| 4,287,347 | 9/1981 | Fah et al. | 546/345 |

OTHER PUBLICATIONS

Kosorotov et al., Zhurnal Organicheskoi Khimii, vol. 16, No. 10, pp. 2163–2171 (Oct. 1980) (English language translation).

*Primary Examiner*—Henry R. Jiles
*Assistant Examiner*—Robert C. Whittenbaugh
*Attorney, Agent, or Firm*—Graybeal & Cullom

[57] ABSTRACT

Production of polychloropyridine reaction product rich in 2,3,5-trichloropyridine by non-catalytic liquid phase chlorination of 3,5-dichloro-2-trichloromethyl pyridine at a temperature in the range from about 170° to about 220° C.

2,3,5-Trichloropyridine is useful and an intermediate for the preparation of agricultural chemicals, especially herbicides.

4 Claims, 1 Drawing Figure

PROCESS FOR PRODUCING 2,3,5-TRICHLOROPYRIDINE

CROSS-REFERENCE TO RELATED APPLICATION

This application is a continuation-in-part of our co-pending U.S. application Ser. No. 422,752, filed Sept. 4, 1982 now abandoned and entitled "Process For Producing 2,3,5-Trichloropyridine."

BACKGROUND OF THE INVENTION

1. Field of the Invention

The present invention relates to preparation of mixtures rich in 2,3,5-trichloropyridine by non-catalytic chlorination of 3,5-dichloro-2-trichloromethyl pyridine in the absence of ultraviolet (UV) radiation. 2,3,5-trichloropyridine is useful as an intermediate for preparation of agricultural chemicals, especially herbicides.

2. Description of the Prior Art

Fah et al U.S. Pat. No. 4,287,347 describes a process for making 2,3,5-trichloropyridine by reacting 3,5-dichloro-2-pyridone with phosgene. Johnston et al U.S. Pat. No. 3,186,994 discloses the preparation of polychloropyridines by chlorination of chloro-2-trichloromethyl pyridines at temperatures in excess of 160° C., but no mention is made of preparing 2,3,5-trichloropyridine by the process. According to this patent, chlorination of 3,5-dichloro-2-trichloromethyl pyridine at temperatures between 190° C. and 210° C. yields 2,3,5,6-tetrachloropyridine. In Johnston et al U.S. Pat. No. 3,418,323, a process for producing 2,3,5-trichloro-6-trichloromethyl pyridine is taught by chlorination of 3,5-dichloro-2-trichloromethyl pyridine at temperatures from 135° C. to 145° C.

Kosorotov et al, Zhurnal Organicheskoi Khimii, Vol. 16, pp. 2163-2171 (October 1980) appears to teach the production of 2,3,5-trichloropyridine by photochemical chlorination under UV irradiation of 3,5-dichloro-2-trichloromethyl pyridine at 150° C. as a result of the elimination of $CCl_3$ (dealkylation) with substitution by a chlorine atom.

SUMMARY OF THE INVENTION

It has been discovered that mixtures rich in 2,3,5-trichloropyridine may be prepared by non-catalytic chlorination of 3,5-dichloro-2-trichloromethyl pyridine in the liquid phase at temperatures from about 170° C. to about 220° C. in the absence of UV radiation. Yields in excess of 20% of 2,3,5-trichloropyridine by weight, based on the converted 3,5-dichloro-2-trichloromethyl pyridine, have been achieved. It has also been discovered that temperature and residence time are key variables in maximizing the yield of 2,3,5-trichloropyridine.

2,3,5-trichloropyridine has utility, for example, as an intermediate in the preparation of herbicides such as those described in Takahashi et al U.S. Pat. No. 4,092,151 and Orvik U.S. Pat. No. 4,275,212.

DESCRIPTION OF THE PREFERRED EMBODIMENTS

EXAMPLE 1

Figure 1:
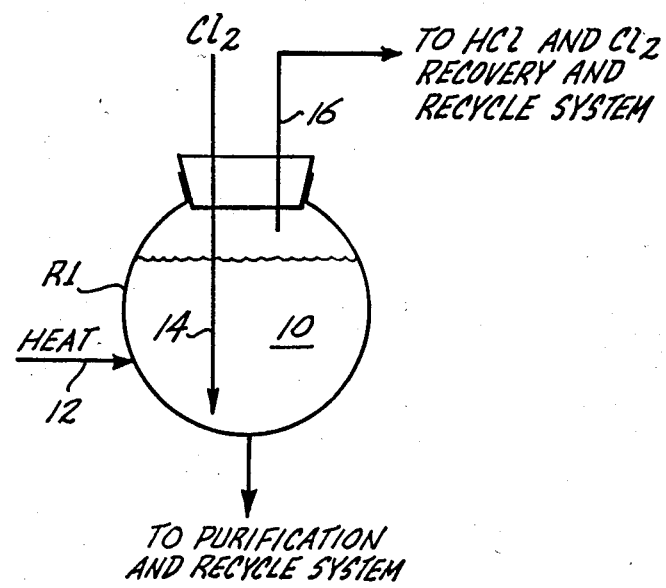
FIG. 1 is a schematic diagram illustrating a system for batch chlorination according to the present invention.

A batch liquid phase chlorination system appears to be the best mode of operation for practice of the present invention in order to obtain maximum yields of 2,3,5-trichloropyridine. FIG. 1 illustrates such a system schematically. As an example of such practice of the invention, and with reference to FIG. 1, 100 grams of 3,5-dichloro-2-trichloromethyl pyridine was charged as charge 10 to batch reactor R1 and the charge brought to a temperature of 200° C. by application of heat as schematically indicated at 12. Chlorine gas flow was started through sparger 14 placed near the bottom of reactor R1. The chlorine flow was maintained at a flow rate so that at least a 50% excess of chlorine was present in the vent line 16 from the reactor R1. The reaction was allowed to proceed under such reaction conditions and gas chromatography analyses were made of the reaction product on an hourly basis. It was found that the optimum yield of 2,3,5-trichloropyridine occurred after the reaction had proceeded for a period of 23 hours, at which time there was about a 29.8% by weight conversion of the 3,5-dichloro-2-trichloromethyl pyridine to other chlorinated components. The reaction mixture was withdrawn from the reactor R1 through discharge line at this time and, by fractional distillation in a manner known per se, the desired 2,3,5-trichloropyridine reaction product was separated. Analysis of the reaction product showed that the yield of 2,3,5-trichloropyridine was 25% of the reacted 3,5-dichloro-2-trichloromethyl pyridine.

As will be readily understood by those skilled in the art to which the invention is addressed, the other chlorinated components in the reaction product are also recoverable in the course of the fractional distillation of the reaction product, and the unreacted 3,5-dichloro-2-trichloromethyl pyridine may be recycled to the next batch, if desired. As also known per se with respect to this type of reaction, the outgases from vent line 16, comprised principally of excess chlorine, and hydrogen chloride as a by-product of the chlorination reaction, are passed to a recovery and recycle system, conventional per se, for separation of the chlorine and recycling thereof to the reaction, and for recovery of the hydrogen chloride.

EXAMPLE 2

The batch reactor utilized in Example 1 was charged with 100 grams of a chloropyridine mixture which contained 98.2% by weight of 3,5-dichloro-2-trichloromethyl pyridine. Excess chlorine was sparged through the reactor R1 by means of sparger 14 for 15 hours at a reaction temperature of 200° C. Analytical samples were taken and analyzed by gas chromatography. The run was then continued at a temperature of 200° C. with continued chlorination for two additional 8 hour periods with additional samples taken at the end of each additional period. The reactor temperature was then raised to 220° C. and the chlorination continued for two additional 8 hour periods with samples being taken at the end of each such additional period. The analyses of the reaction product at the end of each such period is shown by the following Table ONE:

TABLE ONE

Chlorination Times and Temperatures

| Constituent Compound | Initial Analysis (By Weight) | 15 hrs @ 200° C. | 23 hrs @ 200° C. | 31 hrs @ 200° C. | 31 hrs @ 200° C. + 8 hrs @ 220°C. | 31 hrs @ 200° C. + 16 hrs @ 220° C. |
|---|---|---|---|---|---|---|
| 2,3,5-trichloropyridine (Cl at 2,3,5) | 0.2% | 4.8% | 7.7% | 10.6% | 13.4% | 14.6% |
| 3,5-dichloro-2-trichloromethyl pyridine (Cl at 3,5; CCl$_3$ at 2) | 98.2 | 80.0 | 68.4 | 54.2 | 33.9 | 25.1 |
| 2,3,5,6-tetrachloropyridine (Cl at 2,3,5,6) | 1.4 | 2.1 | 4.1 | 7.6 | 16.5 | 23.3 |
| 3,5,6-trichloro-2-trichloromethyl pyridine (Cl at 3,5,6; CCl$_3$ at 2) | 0.2 | 13.0 | 19.8 | 27.6 | 36.2 | 36.9 |

The maximum yield of 2,3,5-trichloropyridine occurred in the analytical samples taken at the end of 23 hours of chlorination and was about 25% of the 29.8% of the 3,5-dichloro-2-trichloromethyl pyridine which reacted. Yield calculation: 7.5% (the net increase of 2,3,5-trichloropyridine) [the difference between 7.7% and 0.2%] divided by 29.8% (the net decrease of 3,5-dichloro-2-trichloromethyl pyridine) [the difference between 98.2% and 68.4%].

EXAMPLE 3

The batch chlorinator R1 was charged with 50 grams of starting material containing 90.4% 3,5-dichloro-2-trichloromethyl pyridine by weight, and chlorine was sparged through the reactor by means of sparger 14 for 15 hours at a reaction temperature of 170° C. Samples were taken at the time which corresponded to about 14% conversion of the 3,5-dichloro-2-trichloromethly pyridine. The yield of 2,3,5-trichloropyridine at this temperature, was about 14%, i.e., about half the yield of like runs at 200° C. (Table ONE). The chlorination was then continued under the same reaction conditions except at a temperature of 160° C. and yielded no appreciable quantity of 2,3,5-trichloropyridine in 8 hours. Analytical data with respect to this Example are presented in the following Table TWO:

TABLE TWO

| Constituent Compound | Initial Analysis (by weight) | 15 hrs @ 170° C. | 15 hrs @ 170° C. + 8 hrs @ 160° C. |
|---|---|---|---|
| 2,3,5-trichloropyridine | 1.2% | 2.9% | 2.9% |
| 3,5-dichloro-2-trichloromethyl pyridine | 90.4 | 78.2 | 78.2 |
| 2,3,5,6-tetrachloropyridine | 1.1 | 2.3 | 2.3 |
| 3,5,6-trichloro-2-trichloromethyl pyridine | 7.1 | 16.6 | 16.6 |

As will be understood by those skilled in the art to which the invention is addressed, processing variations can be employed within the scope of the present invention. For example, rather than performing the chlorination reaction in a single stage batch reactor, a multi-stage continuous system of a type known per se can be employed with total residence time of the liquid phase in the reactors controlled as a function of temperature to optimize the yield of 2,3,5-trichloropyridine. It is considered, however, that a batch-type system is preferable because the time of reaction for all reactant constituents can be more closely controlled when the chlorination reaction proceeds in a single reactor.

What is claimed is:

1. The process of producing a polychloropyridine mixture rich in 2,3,5-trichloropyridine by non-catalytically chlorinating 3,5-dichloro-2-trichloromethyl pyridine in the liquid phase, said process comprising:

(a) establishing in a reactor means an initial charge which is at least principally 3,5-dichloro-2-trichloromethyl pyridine;

(b) while maintaining the reactor charge in the liquid phase and at a temperature in the range of from about 170° C. to about 220° C., sparging excess chlorine into the reactor charge near the bottom thereof in the absence of a catalyst and in the absence of ultraviolet radiation, said chlorine feed rate being sufficient to ensure that at least 50% excess chlorine is maintained in the outgas from the reactor; and (c) continuing chlorine addition and heating of the reactor charge under the indicated conditions until at least about 20% by weight of the 3,5-dichloro-2-trichloromethyl pyridine is converted to 2,3,5-trichloropyridine.

2. The process of claim 1, further comprising thereafter removing the reaction mass from the reactor and separating the 2,3,5-trichloropyridine from the other chlorinated components of the reaction mass.

3. The process of claim 1, comprising continuing the chlorination at a temperature of about 200° C. for at least about 31 hours and then at about 220° C. for at least about 8 hours, with at least about 20% by weight of the 3,5-dichloro-2-trichloromethyl pyridine being converted to a mixture rich in 2,3,5-trichloropyridine.

4. The process of claim 1, comprising continuing the chlorination for a period of time at an initial temperature within the reactor and then for an additional period of time at a higher temperature in order to produce larger quantities of 2,3,5-trichloropyridine.

* * * * *